(12) United States Patent
Sharratt et al.

(10) Patent No.: US 9,944,578 B2
(45) Date of Patent: Apr. 17, 2018

(54) PROCESS FOR THE PREPARATION OF HALOGENATED ALKENES BY DEHYDROHALOGENATION OF HALOGENATED ALKANES

(71) Applicant: MEXICHEM AMANCO HOLDING S.A. DE C.V., Tlalnepantla (MX)

(72) Inventors: Andrew Paul Sharratt, Cheshire (GB); Claire Nicola Rees, Cheshire (GB); Maxine Doran, Cheshire (GB)

(73) Assignee: MEXICHEM AMANCO HOLDING S.A. DE C.V., Tlalnepantla (MX)

( * ) Notice: Subject to any disclaimer, the term of this patent is extended or adjusted under 35 U.S.C. 154(b) by 0 days.

(21) Appl. No.: 15/329,392

(22) PCT Filed: Jul. 27, 2015

(86) PCT No.: PCT/GB2015/052165
§ 371 (c)(1),
(2) Date: Jan. 26, 2017

(87) PCT Pub. No.: WO2016/016625
PCT Pub. Date: Feb. 4, 2016

(65) Prior Publication Data
US 2017/0253543 A1    Sep. 7, 2017

(30) Foreign Application Priority Data
Jul. 28, 2014  (GB) ................................ 1413340.9

(51) Int. Cl.
| | |
|---|---|
| *C07C 17/25* | (2006.01) |
| *B01J 23/755* | (2006.01) |
| *B01J 23/92* | (2006.01) |
| *B01J 23/96* | (2006.01) |
| *B01J 23/90* | (2006.01) |
| *B01J 23/94* | (2006.01) |
| *B01J 21/20* | (2006.01) |

(52) U.S. Cl.
CPC .............. *C07C 17/25* (2013.01); *B01J 21/20* (2013.01); *B01J 23/755* (2013.01); *B01J 23/90* (2013.01); *B01J 23/92* (2013.01); *B01J 23/94* (2013.01); *B01J 23/96* (2013.01)

(58) Field of Classification Search
CPC combination set(s) only.
See application file for complete search history.

(56) References Cited

U.S. PATENT DOCUMENTS

| | | | | |
|---|---|---|---|---|
| 5,202,102 | A * | 4/1993 | Nguyen | .................... B01J 37/24 208/262.1 |
| 8,536,388 | B2 * | 9/2013 | Smith | .................... C07C 17/087 570/155 |
| 2009/0043136 | A1 * | 2/2009 | Wang | ....................... B01J 27/10 570/136 |
| 2013/0211155 | A1 | 8/2013 | Nair et al. | |
| 2013/0211156 | A1 | 8/2013 | Nair et al. | |
| 2014/0005446 | A1 | 1/2014 | Imura et al. | |

FOREIGN PATENT DOCUMENTS

| | | | | |
|---|---|---|---|---|
| GB | | 2228426 A * | 8/1990 | .............. B01J 8/125 |
| WO | WO2009/009421 | | 1/2009 | |
| WO | WO2009/021154 | | 2/2009 | |
| WO | WO2013/055726 | | 4/2013 | |
| WO | WO2014/150889 | | 9/2014 | |

* cited by examiner

*Primary Examiner* — Medhanit W Bahta
(74) *Attorney, Agent, or Firm* — Ryan Kromholz & Manion, S.C.

(57) ABSTRACT

The present invention provides a process for the preparation of a (hydro)(chloro)fluoroalkene by contacting a reagent stream comprising a hydrochlorofluoroalkane with a catalyst in a reactor to dehydrochlorinate at least a portion of the hydrochlorofluoroalkane to produce a product stream comprising the (hydro)(chloro)fluoroalkene and hydrogen chloride (NCI), wherein the catalyst is selected from the group consisting of metal oxide catalysts, metal halide catalysts, zero-valent metal catalysts, carbon-based catalysts and mixtures thereof, and wherein (i) the catalyst is chlorinated prior to contacting it with the reagent stream comprising the hydrochlorofluoroalkane; and/or (ii) the contacting step is carried out in the presence of a HCI co-feed.

26 Claims, No Drawings

PROCESS FOR THE PREPARATION OF HALOGENATED ALKENES BY DEHYDROHALOGENATION OF HALOGENATED ALKANES

This application is the U.S. National Phase under 35 U.S.C. § 371 of International Application No. PCT/GB2015/052165, filed Jul. 27, 2015, designating the United States and published in English on Feb. 4, 2016, as WO 2016/016625, which claims priority to United Kingdom Application No. 1413340.9, filed Jul. 28, 2014, each of which is incorporated by reference in its entirety.

FIELD

The present invention relates to a process for preparing (hydro)(chloro)fluoroalkenes and particularly to a process for preparing (hydro)(chloro)fluoroalkenes by the catalytic dehydrohalogenation of hydrochlorofluorocarbons.

BACKGROUND

The listing or discussion of information or a prior-published document in this specification should not necessarily be taken as an acknowledgement that the information or document is part of the state of the art or is common general knowledge.

(Hydro)(chloro)fluoroalkenes such a (hydro)(chloro)fluoropropenes can be prepared from corresponding hydrochlorofluoroalkanes by dehydrochlorination. The transformation can be effected thermally, i.e. by pyrolysis, catalytically, by contacting a hydrochlorofluoroalkane with a catalyst under suitable conditions, or chemically, typically by contacting a hydrochlorofluoroalkane with strong bases such as alkali metal hydroxides.

However, the preparation of (hydro)(chloro)fluoroalkenes, for example via catalytic dehydrochlorination, often is problematic due to competing dehydrofluorination reactions. Competing dehydrofluorination reactions may produce unwanted by-products that must be removed or recycled. As a result, dehydrochlorination reactions typically have lower than desired selectivity for the target (hydro)(chloro)fluoroalkene products.

Thus, there is a need for a process that suppresses any undesirable and competing dehydrofluorination reaction and correspondingly increases selectivity for the target (hydro)(chloro)fluoroalkene. Such a process would increase both the yield of the desired (hydro)(chloro)fluoroalkene product and the single-pass productivity of the reaction.

SUMMARY

The invention addresses the foregoing and other deficiencies by the provision of a process for the preparation of a (hydro)(chloro)fluoroalkene by contacting a reagent stream comprising a hydrochlorofluoroalkane with a catalyst in a reactor to dehydrochlorinate at least a portion of the hydrochlorofluoroalkane to produce a product stream comprising the (hydro)(chloro)fluoroalkene and hydrogen chloride (HCl), wherein the catalyst is selected from the group consisting of metal oxide catalysts, metal halide catalysts, zero-valent metal catalysts, carbon-based catalysts and mixtures thereof, and wherein (i) the catalyst is chlorinated prior to contacting it with the reagent stream comprising the hydrochlorofluoroalkane; and/or (ii) the contacting step is carried out in the presence of a HCl co-feed.

DETAILED DESCRIPTION

The (Hydro)(Chloro)Fluoroalkene and Hydrochlorofluoroalkane

Preferably, the process of the invention is directed to the preparation of a $C_{3-7}$ (hydro)(chloro)fluoroalkene by dehydrochlorinating a corresponding $C_{3-7}$ hydrochlorofluoroalkane.

Advantageously, the $C_{3-7}$ (hydro)(chloro)fluoroalkene prepared by the process of the invention is a (hydro)(chloro)fluorobutene or a (hydro)(chloro)fluoropropene. In one embodiment, therefore, the process of the invention is directed to the preparation of a (hydro)(chloro)fluoropropene by dehydrochlorinating a corresponding hydrochlorofluoropropane.

For clarity and conciseness, unless otherwise stated, the remainder of this specification is concerned with the preparation of (hydro)(chloro)fluoropropenes. Of course, it is to be understood that the invention is not limited to the preparation of (hydro)(chloro)fluoropropenes and that any of the foregoing information is applicable, where appropriate, to the preparation of $C_{4-7}$ and higher (hydro)(chloro)fluoroalkenes.

By the term (hydro)(chloro)fluoropropene we include hydrochlorofluoropropenes, hydrofluoropropenes and perfluoropropene. Similarly, by the term (hydro)(chloro)fluoroalkene we include hydrochlorofluoroalkenes, hydrofluoroalkenes and perfluoroalkenes and by the term (hydro)(chloro)fluorobutene we include hydrochlorofluorobutenes, hydrofluorobutenes and perfluorobutene.

Preferred hydrochlorofluoropropenes that can be prepared by the process of the invention include trifluorochloropropenes such as 1-chloro-3,3,3-trifluoropropene ($CF_3CH$=$CHCl$, HCFO-1233zd) and 2-chloro-3,3,3-trifluoropropene ($CF_3CCl$=$CH_2$, HCFO-1233xf).

HCFO-1233zd can be prepared in the accordance with the process of the invention by dehydrochlorinating 1,2-dichloro-3,3,3-trifluoropropane ($CF_3CHClCH_2Cl$, HCFC-243db) and/or 1,1-dichloro-3,3,3-trifluoropropane ($CF_3CH_2CHCl_2$, HCFC-243fa). Preferably, HCFO-1233zd is prepared by dehydrochlorinating HCFC-243fa. For the avoidance of doubt, we include both the cis and trans isomers of HCFO-1233zd within the scope of the invention.

HCFO-1233xf can be prepared in the accordance with the process of the invention by dehydrochlorinating 1,2-dichloro-3,3,3-trifluoropropane ($CF_3CHClCH_2Cl$, HCFC-243db) and/or 2,2-dichloro-3,3,3-trifluoropropane ($CF_3CCl_2CH_3$, HCFC-243cb). Preferably, HCFO-1233xf is prepared by dehydrochlorinating 243db.

Hydrofluoropropenes that can be prepared by the process of the invention include trifluoropropenes, tetrafluoropropenes and pentafluoropropenes, preferably trifluoropropenes and tetrafluoropropenes, and particularly tetrafluoropropenes.

3,3,3-trifluoropropene ($CF_3CH$=$CH_2$, HFO-1243zf) is a preferred trifluoropropene that can be prepared in accordance with the invention, by dehydrochlorination of 1-chloro-3,3,3-trifluoropropane ($CF_3CH_2CH_2Cl$, HCFC-253fb) and/or 2-chloro-3,3,3-trifluoropropane ($CF_3CHClCH_3$, HCFC-253da). Preferably, HFO-1243zf is prepared by dehydrochlorinating 253fb.

1,3,3,3-tetrafluoropropene ($CF_3CH$=$CHF$, HFO-1234ze) is a preferred tetrafluoropropene that can be prepared in accordance with the invention, by dehydrochlorination of 1-chloro-1,3,3,3-tetrafluoropropane ($CF_3CH_2CHClF$, HCFC-244fa) and/or 2-chloro-1,3,3,3-tetrafluoropropane ($CF_3CHClCH_2F$, HCFC-244db). Preferably, HFO-1234ze is prepared by dehydrochlorinating 244fa. For the avoidance of doubt, we include both the cis and trans isomers of HFO-1234ze within the scope of the invention.

2,3,3,3-tetrafluoropropene ($CF_3CH=CHF$, HFO-1234yf) is another preferred tetrafluoropropene that can be prepared in accordance with the invention, by dehydrochlorination of 1-chloro-2,3,3,3-tetrafluoropropane ($CF_3CHFCH_2Cl$, HCFC-244eb) and/or 2-chloro-2,3,3,3-tetrafluoropropane ($CF_3CFClCH_3$, HCFC-244bb). Preferably, HFO-1234yf is prepared by dehydrochlorinating 244bb.

Pentafluoropropenes that can be prepared in accordance with the process of the invention include 1,2,3,3,3-pentafluoropropene ($CF_3CF=CFH$, HFO-1225ye) and 1,1,3,3,3-pentafluoropropene ($CF_3CH=CF_2$, HFO-1225zc). HFO-1225ye is a preferred pentafluoropropene that can be prepared by dehydrochlorination of 2-chloro-1,2,3,3,3-pentafluoropropane ($CF_3CFClCH_2F$, HCFC-235bb) and/or 1-chloro-1,2,3,3,3-pentafluoropropane ($CF_3CFHCHFCl$, HCFC-235ea). For the avoidance of doubt, we include both the cis and trans isomers of HFO-1225ye within the scope of the invention.

Perfluoropropene ($CF_3CF=CF_2$, 1216) may be prepared in accordance with the process of the invention by dehydrochlorinating 2-chloro-1,1,2,3,3,3-hexafluoropropane ($CF_3CFClCF_2H$, HCFC-226ba) and/or 1-chloro-1,1,2,3,3,3-hexafluoropropane ($CF_3CFHCF_2Cl$, HCFC-226ea).

The Catalyst

The catalyst used in the process of the invention comprises one or more of (a) a metal oxide, (b) a metal halide, (c) a zero-valent metal or (d) carbon-based catalyst. In one aspect of the invention, the catalyst comprises one or more of (a) a metal oxide, (b) a metal halide, or (c) a zero-valent metal. In an embodiment, the catalyst comprises one or more of (a) a metal oxide or (b) a metal halide. Preferably, the catalyst comprises a metal oxide.

As explained in more detail below, in use, each of the four categories of catalyst will be at least partially chlorinated. So, for instance, the metal oxide catalyst in use can be considered to be a metal (oxy)chloride (typically a metal oxychloride), and the metal halide catalyst can be considered to be a metal (halo)chloride. Optionally, the catalyst is fluorinated prior to chlorination in use or pre-chlorination. The catalyst in use may also become fluorinated by any HF present due to competing dehydrofluorination of the hydrochlorofluoroalkane. In use, therefore, each of the four categories of catalyst will be at least partially chlorinated and may also be at least partially fluorinated. Thus, for example, the metal oxide catalyst in use can be considered to be a metal (oxy)(fluoro)chloride, typically a metal oxyfluorochloride.

The form of the catalyst can vary, depending on, for example, the nature of the catalyst and/or the particular (hydro)(chloro)fluoropropene being prepared. The catalyst may contain components added to improve the activity, stability and/or ease of preparation of the catalyst. See, for example, the discussions below regarding promoters that may be used in metal oxide catalysts. Alternatively/additionally, the catalyst may contain a binder and/or a lubricant to improve the physical integrity of the catalyst when shaping or granulating the catalyst into a desired from. Magnesium stearate is an example of a suitable lubricant/binder. Another suitable lubricant/binder is graphite. If present, the binder and/or lubricant typically is present in an amount of from about 0.1 to about 10% by weight of the catalyst, preferably from about 0.2 to about 6% by weight of the catalyst.

The catalysts used herein can be unsupported or supported on any suitable substrate. See, for example, "The design and Preparation of Supported Catalysts", G. J. K. Acres et al, Catalysis, 1981 (RSC), which is incorporated herein by reference, regarding suitable catalyst supports. Typical catalyst supports include, for example, activated carbon, graphite, chlorinated graphite and combinations thereof. As described later in this specification, in addition to being suitable catalyst supports, activated carbon and graphite are also suitable catalysts in their own right for the process of the invention. The catalyst of the invention can be provided in any suitable form including, for example, pellets or granules of appropriate size for use in a fixed bed or a fluidised bed.

The first category of catalyst suitable for use in the process of the invention is a catalyst comprising a metal oxide. Typically, the metal in the metal oxide catalyst is one or more of any metal which forms a metal (oxy)chloride or metal (oxy)(fluoro)chloride which has Lewis acid character. Examples are metals selected from Li, Na, K, Ca, Mg, Cs, Al, Sc, Y, Ti, Zr, Hf, V, Nb, Ta, Cr, Mo, W, Mn, Re, Fe, Ru, Co, Rh, Ir, Ni, Pd, Pt, Cu, Ag, Au, Zn, La and Ce. In one embodiment, the metal in the metal oxide is selected from Li, Na, K, Ca, Mg, Cs, Cr, Al, Zr, Nb, Pd, Ta, Zn, V, Mo, Ni, Co and mixtures thereof. In another embodiment, the metal in the metal oxide is a transition metal selected from Cr, Zr, Nb, Ta, V, Mo, Pd, Ni, Zn, Co (especially Cr and Zn) and mixtures thereof. In a further embodiment, the metal in the metal oxide is a group I or II metal selected from Li, Na, K, Ca, Mg and Cs. Examples of preferred metal oxides include $Cr_2O_3$, $ZrO_2$, $Li_2O$, $Na_2O$, $K_2O$, CaO, MgO, $Cs_2O$ and mixtures thereof. Catalysts based on $Cr_2O_3$ (chromia) are especially preferred in certain embodiments.

In use, the metal oxide catalyst typically is a metal (oxy)(fluoro)chloride. This is because at least some of the oxygen in the lattice of the metal oxide, or the metal (oxy)fluoride (if the metal oxide is pre-fluorinated and/or the catalyst is fluorinated by HF in use), is replaced by chlorine by the pre-chlorination step and/or by the co-feed of HCl according to the process of the invention. Put another way, the metal oxide (or the metal (oxy)fluoride if the metal oxide is pre-fluorinated) can be considered to be a pre-catalyst.

The metal oxide catalyst used in the process of the invention may contain at least one additional metal or compound thereof. This can also be referred to as a metal promoter. In one embodiment, the at least one additional metal is selected from Li, Na, K, Ca, Mg, Cs, Sc, Al, Y, Ti, Zr, Hf, V, Nb, Ta, Cr, Mo, W, Mn, Re, Fe, Ru, Co, Rh, Ir, Ni, Pd, Pt, Cu, Ag, Au, Zn, La, Ce and mixtures thereof. Preferably, the at least one additional metal is selected from Li, Na, K, Ca, Mg, Cs, Cr, Zr, Nb, Pd, Ta, Zn, V, Mo, Ni, Co and mixtures thereof.

For the avoidance of doubt, the additional metal (or compound thereof) cannot be the same as the metal in the same oxidation state of the metal oxide for any given catalyst. For example, if the catalyst comprises an oxide of chromium (III), the at least one additional metal can be any suitable metal, including the metals listed in the preceding paragraph, other than chromium (III). Moreover, if the catalyst comprises an oxide of chromium (III), the at least one additional metal (or compound thereof) can be a compound of chromium (VI). In a preferred aspect, the compound of the additional metal is an oxide, chloride or oxychloride of the additional metal. A preferred additional metal for $Cr_2O_3$-based catalysts is zinc or a compound of zinc. Such zinc-promoted chromia catalysts are often referred to as zinc/chromia catalysts.

When present, the total amount of the additional metal or the compound of the additional metal present in the catalysts of the invention is typically from about 0.01% to about 25% by weight, based on the total weight of the catalyst. Preferred amounts of the additional metal or the compound of additional metal are from about 0.1% to about 20%, conveniently from about 0.1% to about 15%. In some embodiments, the catalysts contain the additional metal or the compound of additional metal in an amount of from about 0.5% by weight to about 10% by weight of the catalyst, such as from about 1 to about 8% by weight of the catalyst, e.g. about 1 to about 5% by weight.

It is to be understood that the amount of additional metal or the compound of the additional metal quoted herein refers to the amount of elemental metal, whether present as elemental metal or as a compound of the metal.

The metal oxide catalyst used in the invention may be commercially available and/or can be prepared by any suitable means. Metal oxide catalysts typically are prepared by precipitation methods whereby the metal oxide of interest is precipitated from a solution of a salt of the metal of interest upon treatment with an alkali or base. For example, chromium (III) oxide can be prepared by precipitation upon treatment of solution chromium (III) nitrate salts with aqueous ammonia. Such a metal oxide catalyst is produced commercially, for example by BASF and Johnson-Matthey.

By way of example only, summarised below are suitable methods for preparing the zinc/chromia catalysts that may be used in the process of the invention. Further details of zinc/chromia catalysts and their preparation may be found in, for example, EP-A-0502605, EP-A-0773061, EP-A-0957074, WO 98/10862 and WO 2008/040969, which are incorporated by reference herein.

Suitable methods for zinc/chromia catalyst preparation include co-precipitation from solutions of zinc and chromium nitrates on the addition of ammonium hydroxide. Alternatively, surface impregnation of the zinc or a compound thereof onto an amorphous chromia catalyst can be used.

Further methods for preparing zinc/chromia catalysts include, for example, reduction of a chromium (VI) compound, for example a chromate, dichromate, in particular ammonium dichromate, to chromium (III), by zinc metal, followed by co-precipitation and washing; or mixing as solids, a chromium (VI) compound and a compound of zinc, for example zinc acetate or zinc oxalate, and heating the mixture to high temperature in order to effect reduction of the chromium (VI) compound to chromium (III) oxide and oxidise the compound of zinc to zinc oxide.

The zinc may be introduced into and/or onto the chromia catalyst in the form of a compound, for example a nitrate, halide, oxyhalide, oxide or hydroxide depending at least to some extent upon the catalyst preparation technique employed. In the case where catalyst preparation is by impregnation of a chromia, halogenated chromia or chromium oxyhalide, the compound is preferably a water-soluble salt, for example a halide, nitrate or carbonate, and is employed as an aqueous solution or slurry. Alternatively, the hydroxides of zinc and chromium may be co-precipitated (for example by the use of a base such as sodium hydroxide, potassium hydroxide or ammonium hydroxide or mixtures of such bases) and then converted to the oxides to prepare the zinc/chromia catalyst. Mixing and milling of an insoluble zinc compound with the basic chromia catalyst provides a further method of preparing the catalyst precursor. A method for making a zinc/chromia catalyst based on chromium oxyhalide comprises adding a compound of zinc to hydrated chromium halide.

The second category of catalyst suitable for use in the process of the invention is a catalyst comprising a metal halide. The halide in the metal halide catalyst can be any halide selected from fluoride, chloride, bromide and iodide, preferably fluoride or chloride. However, in use a metal fluoride, bromide or iodide will be a metal (halo)chloride (where halo=fluoride, bromide or iodide). This is because at least some of the halide in the lattice of the metal halide is replaced by chlorine by the pre-chlorination step and/or by the co-feed of HCl according to the process of the invention. Optionally, the catalyst undergoes a pre-fluorination step prior to chlorination in the pre-chlorination step and/or by the co-feed of HCl. In such circumstances, and/or because the catalyst can become at least partially fluorinated by any HF present in the reactor as a consequence of competing hydrochlorofluoroalkane dehydrofluorination, the metal halide catalyst in use can be considered to be a metal (fluoro)(halo)chloride (wherein halo=bromide or iodide).

Typically, the metal in the metal halide catalyst is selected from Li, Na, K, Ca, Mg, Cs, Sc, Y, Ti, Zr, Hf, V, Nb, Ta, Cr, Mo, W, Mn, Re, Fe, Ru, Co, Rh, Ir, Ni, Zn, La, Ce and mixtures thereof. In one embodiment, the metal in the metal halide is selected from Li, Na, K, Ca, Mg, Cs and mixtures thereof. In another embodiment, the metal in the metal halide is a transition metal selected from Cr, Zr, Nb, Ta, Fe, V, Mo, Pd, Ni, Zn, Co (especially Cr and Zr) and mixtures thereof.

The metal halide catalyst may be available commercially and/or can be prepared by any suitable means. For example, suitable metal hydroxides, oxides and/or carbonates can be dissolved in an aqueous HCl and/or HF solution in a vessel resistant to corrosion. Following evaporation to dryness, the resulting sample can be calcined at an elevated temperature, preferably in the presence of an inert gas such as nitrogen. Typically, the resulting material is ground to a fine powder and, preferably, formed into pellets or granules.

The third category of catalyst suitable for use in the process of the invention is a catalyst comprising a zero-valent metal. The zero-valent metal catalyst typically comprises a zero-valent metal selected from Fe, Co, Ni, Cu, Mo, Cr, Mn, Pd, Pt, Nb, Rh, and mixtures thereof. Suitable catalysts include palladium supported on (activated) carbon, nickel and alloys of the foregoing metals. Suitable alloys include stainless steel, Monel® and Inconel®. Catalysts comprising Nickel are currently particularly preferred.

In use, the zero-valent metal catalyst typically is at least partially chlorinated by the pre-chlorination step and/or by the co-feed of HCl according to the process of the invention. In use, the zero-valent metal catalyst may also be at least partially fluorinated by any HF produced by competing hydrochlorofluoroalkane dehydrofluorination. Put another way, at least some of the zero-valent metal catalyst in use has a higher valency than zero-valent, thus the zero-valent metal can be considered to be a pre-catalyst. This has the consequence that regeneration of the zero-valent metal catalyst typically requires a reduction step to at least partially reduce metal chloride to zero-valent metal. This is described in more detail later in this specification in connection with catalyst regeneration.

The fourth category of catalyst that may be used in the process of the invention is a carbon-based catalyst. Activated carbon and graphite are examples of suitable carbon-based catalysts. In one embodiment, the carbon-based catalyst comprises activated carbon.

By activated carbon, we include any carbon with a relatively high surface area such as from about 50 to about 3000 m² or from about 100 to about 2000 m² (e.g. from about 200 to about 1500 m² or about 300 to about 1000 m²). The activated carbon may be derived from any carbonaceous material, such as coal (e.g. charcoal), nutshells (e.g. coconut) and wood. Any form of activated carbon may be used, such as powdered, granulated, extruded and pelleted activated carbon.

In use, the carbon-based catalyst typically is at least partially chlorinated by the pre-chlorination step and/or by the co-feed of HCl according to the process of the invention. The carbon-based catalyst may also be at least partially fluorinated in use by any HF produced by competing hydrochlorofluoroalkane dehydrofluorination.

The catalysts used in the present invention may be amorphous. By this we mean that the catalyst does not demonstrate substantial crystalline characteristics when analysed by, for example, X-ray diffraction. Alternatively, the catalysts may exhibit some crystalline character, in the alumina (support) and/or the metal oxide or in the carbon.

For example, the metal oxide and/or metal halide catalyst may be partially crystalline. By this we mean that from 0.1 to 50% by weight of the catalyst is in the form of one or more crystalline compounds of the metal(s) in the catalyst. If a partially crystalline catalyst is used, it preferably contains from 0.2 to 25% by weight, more preferably from 0.3 to 10% by weight, still more preferably from 0.4 to 5% by weight of the catalyst in the form of one or more crystalline compounds of the metal(s) in the catalyst.

Pre-Chlorination of Catalyst and/or Co-Feed of HCl

A key feature of the process of the invention is that (i) the metal-based catalyst is chlorinated prior to contacting the catalyst with the hydrochlorofluoroalkane to catalyse dehydrochlorination, or (ii) the step of contacting the catalyst with the hydrochlorofluoroalkane is carried out in the presence of a HCl co-feed. Alternatively, both the catalyst pre-chlorination step (i) and the HCl co-feed (ii) can be used in the process of the invention. Without being bound by theory, it is believed that depending on the combination of hydrochlorofluoroalkane and reactions conditions etc., one or both of the catalyst pre-chlorination step (i) and the use of a HCl co-feed (ii) surprisingly increases the selectivity for the desired dehydrochlorination over any undesired dehydrofluorination reaction, and/or increases the stability of the catalyst in use.

The catalyst pre-chlorination step (i) can be effected by any suitable chlorination agent, including, for example, diatomic chlorine ($Cl_2$), ClF (e.g. formed in situ as a mixture of $Cl_2$ and hydrogen fluoride) and hydrogen chloride (HCl). In one embodiment, the catalyst is chlorinated with a chlorinating agent comprising HCl and/or or $Cl_2$. Preferably, the chlorinating agent comprises HCl.

The catalysts described herein (particularly the metal oxide catalysts) are typically stabilised by heat treatment before use such that they are stable under the environmental conditions that they are exposed to in use. The catalyst is preferably stabilised by heat treatment in nitrogen or a nitrogen/air environment. In the art, this stage is often called "calcination". Many commercially available catalysts have already been calcined and, in one embodiment, the catalyst pre-chlorination step is carried out on a pre-calcined catalyst.

Alternatively, it is relatively straightforward to incorporate a calcination step prior to the catalyst pre-chlorination. For example, the catalysts (particularly the metal oxide catalysts) may be heat treated in a suitable atmosphere including an atmosphere of nitrogen or an atmosphere having an oxygen level of from about 0.1 to about 10% v/v in nitrogen. Other oxidizing environments could alternatively be used. For example, environments containing suitable oxidizing agents include, but are not limited to, those containing a source of nitrate, $CrO_3$, $O_2$ or $Cl_2$ (for example air). When used, the pre-calcination step can be carried out under the following conditions.

TABLE 1

Catalyst Calcination

|  | Space velocity ($min^{-1}$)* | Time | Temperature |
| --- | --- | --- | --- |
| Typical | About 0.1-20 | about 30 mins to about 24 hours | about 200-600° C. |
| Preferred | about 0.5-10 | about 1-12 hours | about 300-500° C. |
| More preferred | about 1-8 | about 2-8 hours | about 350-450° C. |

*based on a nominal 10 ml charge of catalyst

In one embodiment, the catalyst pre-chlorination step is carried out on a pre-dried catalyst. Alternatively/additionally, it is relatively straightforward to incorporate a drying step at the start of the catalyst pre-chlorination. This can be conveniently carried out in the reactor in which the subsequent dehydrochlorination reaction is to be conducted. This can be achieved by passing an inert gas (e.g. nitrogen) over the catalyst at elevated temperature. For example, the catalyst can be dried under an inert gas with the following space velocities, drying times and temperatures.

TABLE 2

Catalyst Drying

|  | Inert Gas Space velocity ($min^{-1}$)* | Drying time | Drying Temperature |
| --- | --- | --- | --- |
| Typical | about 0.1-20 | about 1-48 hours | about 100-400° C. |
| Preferred | about 0.5-10 | about 2-24 hours | about 120-350° C. |
| More preferred | about 1-8 | about 3-20 hours | about 150-300° C. |

*based on a nominal 10 ml charge of catalyst

In one embodiment, the catalyst pre-chlorination step is carried out on a pre-fluorinated catalyst. Alternatively/additionally, it is relatively straightforward to incorporate a catalyst fluorination step, if desired, at the start of the catalyst pre-chlorination. This can be conveniently carried out in the reactor in which the subsequent dehydrochlorination reaction is to be conducted. This can be achieved by passing a fluorinating agent (e.g. HF), optionally in combination with an inert gas (e.g. nitrogen), over the catalyst at elevated temperature. For example, the catalyst (particularly a metal oxide catalyst) can be pre-fluorinated (particularly with HF) under the following conditions.

TABLE 3

Catalyst Pre-fluorination

|  | Inert gas (when used) space velocity (min$^{-1}$)* | Fluorinating agent space velocity (min$^{-1}$) | Fluorinating time | Fluorinating temperature |
| --- | --- | --- | --- | --- |
| Typical | about 0.1-20 | about 0.1-10 | about 1-48 hours | about 200-550° C. |
| Preferred | about 0.5-10 | about 0.2-5 | about 2-24 hours | about 220-500° C. |
| More preferred | about 1-8 | about 0.3-3 | about 3-20 hours | about 250-450° C. |

*based on a nominal 10 ml charge of catalyst

The pre-chlorination step is typically carried out by passing a gas stream comprising the chlorinating agent over the catalyst at elevated temperature. This can be conveniently carried out in the reactor in which the subsequent dehydrochlorination reaction is to be conducted. The gas stream may be substantially pure chlorinating agent (e.g. HCl and/or Cl$_2$). Alternatively, however, the chlorinating agent may be passed over the catalyst in the presence of an inert gas (e.g. nitrogen), at least initially, to dilute the chlorinating agent. For example, the catalyst (particularly a metal oxide catalyst) can be pre-chlorinated (particularly with HCl) under the following conditions.

TABLE 4

Catalyst Pre-chlorination

|  | Inert gas (when used) space velocity (min$^{-1}$)* | Chlorinating agent space velocity (min$^{-1}$) | Chlorinating time | Chlorinating temperature |
| --- | --- | --- | --- | --- |
| Typical | about 0.1-20 | about 0.1-5 | about 1-48 hours | about 200-600° C. |
| Preferred | about 0.5-10 | about 0.2-3 | about 2-24 hours | about 220-500° C. |
| More preferred | about 1-8 | about 0.3-2 | about 4-20 hours | about 250-450° C. |

*based on a nominal 10 ml charge of catalyst

Catalyst drying, fluorination (when used) and chlorination can be combined into a single procedure. This has the advantage of process economy and simplicity by optimising the catalyst activity, selectivity and stability in a single step. In such a procedure, the catalyst is dried in accordance with the conditions set out in table 2. If the catalyst is fluorinated, fluorinating agent (e.g. HF) is then flowed over the catalyst, often at least initially in addition to the inert gas flow (e.g. N$_2$), in accordance with the conditions set out in Table 3. Flow of the fluorinating agent is then stopped, and typically a flow of inert gas will then be used to purge the catalyst of any residual fluorinating agent. Then chlorinating agent (e.g. HCl) is then flowed over the catalyst, often at least initially in addition to the inert gas flow (e.g. N$_2$), in accordance with the conditions set out in Table 4.

In the above catalyst chlorination procedure, the inert gas flow typically is switched off following a defined period after the chlorinating agent flow is switched on, for example about 10 minutes to about 20 hours, preferably from about 30 minutes to about 20 hours, for example from about 1 hour to about 12 hours after the chlorinating agent flow is switched on. Alternatively, once the chlorinating agent is detected in the off-gas from the chlorination, the inert gas flow can be switched off. Typically, the temperature of the reactor is then increased (see the temperature ranges in Table 2 compared to Table 3) to facilitate catalyst chlorination. Optionally, when catalyst pre-chlorination is complete, the flow of chlorinating agent can be switched off and the inert gas flow can be re-started to purge the catalyst of any residual chlorinating agent.

Of course, even when the catalyst chlorination is not combined with catalyst drying (and optionally catalyst fluorination) in a single procedure, i.e. when a pre-dried (and optionally pre-fluorinated) catalyst is chlorinated, the chlorinating agent (e.g. HCl) can be diluted with an inert gas (e.g. nitrogen) during catalyst chlorination. Comparative amounts of chlorinating agent and inert gas diluent typically fall within the ranges defined above in Table 3.

As an alternative or in addition to catalyst pre-chlorination, the dehydrochlorination process of the invention can be carried out in the presence of a co-feed of HCl. Put another way, during the step of contacting the reagent stream comprising the hydrochlorofluoroalkane with the catalyst to dehydrochlorinate at least a portion of the hydrochlorofluoroalkane, a feed of HCl can be fed to the reactor. The HCl can be fed separately to the reactor and/or combined with the hydrochlorofluoroalkane in the reagent stream.

For the avoidance of doubt, the HCl co-feed, when used, increases the amount of HCl present in the reactor over and above that present in the reactor in situ from the dehydrochlorination of the hydrochlorofluoroalkane. Indeed, in one embodiment, at least a portion of the HCl produced by the dehydrochlorination of the hydrochlorofluoroalkane is recycled to the dehydrochlorination reactor to form at least a portion of the HCl co-feed.

In one aspect, at least a portion of the HCl co-feed originates from a preceding process step of manufacturing the hydrochlorofluoroalkane. Typically, the hydrochlorofluoroalkane that forms part of the reagent stream in the process of the invention is prepared by fluorination of a (hydro)chloro(fluoro)alkane or (hydro)chloro(fluoro)alkene, preferably a hydrochloro(fluoro)alkane or hydrochloro(fluoro)alkene.

For example, HCFC-243fa and HCFC-244fa can be prepared by fluorination of 1,1,1,3,3,-pentachloropropane (HCC-240fa) with HF according to the following equations:

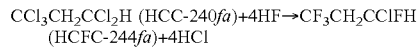

$$CCl_3CH_2CCl_2H \; (HCC\text{-}240fa) + 4HF \rightarrow CF_3CH_2CClFH \; (HCFC\text{-}244fa) + 4HCl$$

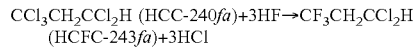

$$CCl_3CH_2CCl_2H \; (HCC\text{-}240fa) + 3HF \rightarrow CF_3CH_2CCl_2H \; (HCFC\text{-}243fa) + 3HCl$$

At least a portion of HCl produced in the preparation of the hydrochlorofluoroalkane can be used in the HCl co-feed in the process of the invention. So, in the above examples, at least a portion of the HCl produced in the preparation of HCFC-244fa can be used in a co-feed in the process of the invention for dehydrochlorinating HCFC-244fa to HFO-1234ze. Similarly, at least a portion of the HCl produced in the preparation of HCFC-243fa can be used in a co-feed in the process of the invention for dehydrochlorinating HCFC-243fa to HCFO-1233zd.

When a HCl co-feed is used, the amount of HCl fed to the dehydrochlorination reactor typically is up to about 50 mol %, based on the combined amount of hydrochlorofluoroalkane and HCl. In one embodiment, the amount of HCl fed to the dehydrochlorination reactor is up to about 40 mol %, preferably up to about 30 mol % or about 20 mol %, for example up to about 10 mol %, based on the combined amount of hydrochlorofluoroalkane and HCl. Preferably, the amount of HCl fed to the dehydrochlorination reactor is at least about 1% or about 2%, for example at least about 5%, based on the combined amount of hydrochlorofluoroalkane and HCl.

Without being bound by theory, it is believed that the use of a co-feed of HCl, which increases the concentration of HCl in the reactor, improves (i) the stability and thus lifetime of the catalyst, and/or (ii) the selectivity to the desired (hydro)(chloro)fluoroalkene dehydrochlorination product. The latter is particularly surprising as one might expect an increase in concentration of HCl to retard the dehydrochlorination, and correspondingly the selectivity to the dehydrochlorination product compared to the dehydrofluorination product.

The exact preferred conditions of the process of the invention depend on, for example, the nature of the reagent and product and the catalyst being used. Included hereinbelow is some guidance as to suitable and preferred reaction conditions.

The dehydrochlorination process of the invention typically is carried out at from sub-atmospheric to super-atmospheric pressure, for example from about 0.1 to about 40 bara, such as from about 0.5 to about 20 bara, preferably from about 0.5 to about 10 bara. Advantageously, the dehydrochlorination is carried out at from about 1 to about 5 bara.

Typically, the dehydrochlorination process of the invention is carried out at a temperature of from about 100° C. to about 600° C., such as from about 120° C. to about 500° C., preferably from about 150° C. to about 450° C. Advantageously, the dehydrochlorination is carried out at a temperature of from about 180° C. to about 420° C.

The process of the invention may be carried out in the gas phase or the liquid phase. Generally, the gas phase is preferred, particularly when the catalyst comprises a metal oxide.

The contact time for the for the reagent stream comprising the hydrochlorofluoroalkane and the catalyst can be represented by the space velocity (SV), which is the volumetric flow entering reactor divided by reactor volume. Based on a nominal 10 ml charge of catalyst, the typical SV is from about 0.1 $min^{-1}$ to about 10 $min^{-1}$, preferably from about 0.5 $min^{-1}$ to about 7.5 $min^{-1}$, more preferably from about 1 $min^{-1}$ to about 5 $min^{-1}$.

The process of the invention can be carried out in any suitable apparatus, such as a static mixer, a stirred tank reactor or a stirred vapour-liquid disengagement vessel. The process may be carried out batch-wise, or continuously. Either the batch-wise process or the continuous process may be carried out in a "one-pot" fashion, or using two or more discrete reaction zones and/or reaction vessels. Preferably, the reaction is carried out continuously. Even in a "continuous" process, however, the process will need to be paused periodically, e.g. for maintenance and/or catalyst regeneration.

Catalyst regeneration can be carried out by any suitable means. For example, a metal oxide catalyst (e.g. a chromia-based catalyst) can be regenerated periodically by heating in air at a temperature of from about 300° C. to about 500° C. Air may be used as a mixture with an inert gas such as nitrogen or with the chlorinating agent. Alternatively, the catalyst (e.g. a metal oxide catalyst) can be regenerated continuously whilst in use by introducing an oxidising gas into the reactor e.g. oxygen or chlorine. The above is referred to hereinafter as regenerative oxidation and typically is used to regenerate a coked catalyst to restore, at least in part, the activity of the catalyst.

In one embodiment, the regenerative oxidation is carried out in the presence of a fluorinating agent (e.g. HF) in addition to the oxidising gas (e.g. air). Typically this is carried under conditions defined hereinbefore in connection with catalyst pre-fluorination (see Table 3, for instance). This has the effect of partially fluorinating the catalyst (e.g. a metal oxide catalyst) in addition to restoring the activity of the catalyst by oxidation. The above is referred to hereinafter as regenerative oxyfluorination.

Following regeneration with an oxidant gas it may be preferable to reduce the catalysts to remove any high oxidation state species that remain on or in the catalyst and reactor. This is referred to hereinafter as regenerative reduction. Such regenerative reduction step is preferable when the catalyst comprises a zero-valent metal. The regenerative reduction step can involve treatment with, for example, hydrogen under conditions sufficient to affect the necessary reduction. Alternatively, high oxidation state species can be converted to lower oxidation state species by annealing, that is heating the catalyst to a temperature at which high oxidation state species decompose. For instance chromium (VI) species can be converted to chromium (III) species in this manner.

It may also be desirable following regenerative oxidation and/or regenerative reduction to re-chlorinate the catalyst (e.g. a metal oxide catalyst). The conditions described hereinbefore (see Table 4, for instance) in connection with the pre-chlorination step (i) of the process of the invention are generally suitable for this regenerative chlorination. The regenerative chlorination typically is used to regenerate the catalyst (which may be partially fluoride, e.g. in use and/or by regenerative oxyfluorination) to restore the selectivity for the desired dehydrochlorination over any undesired dehydrofluorination reaction, and/or increase the stability of the catalyst in use.

In one embodiment, for example when the catalyst for the process of the invention comprises a metal oxide, catalyst regeneration comprises both regenerative oxidation and regenerative chlorination. In one aspect, such catalyst regeneration is conducted with regenerative oxidation and regenerative chlorination combined in one regenerative oxychlorination procedure. This has the advantage of process economy and simplicity by restoring the catalyst activity, selectivity and stability in a single step.

Regenerative oxychlorination may be carried out by heating the catalyst in the presence of a gas comprising an oxidising agent and a chlorinating agent. Typically, this is conducted at a temperature of from about 250° C. to about 550° C., preferably from about 300° C. to about 500° C. The oxidising gas may be oxygen or chlorine, preferably oxygen. The chlorinating agent may be chlorine or HCl, preferably HCl. Subject to the temperature ranges described above, the conditions described hereinbefore (see Table 4, for instance) in connection with the pre-chlorination step (i) of the process of the invention are generally suitable for this regenerative oxychlorination, with the space velocities for the oxidising gas falling within the scope of the space velocities described for the chlorinating agent.

In another embodiment, for example when the catalyst for the process of the invention comprises a metal oxide, catalyst regeneration comprises both regenerative oxyfluorination and regenerative chlorination.

The invention is illustrated the following non-limiting Example.

Example

Sintered Ni pellets were produced by reducing $NiF_2$ with $H_2$. The catalyst was then loaded to a reactor and re-reduced in the reactor with $H_2$ prior to starting 244bb flow over the pellets, conditions:

Temp=400° C.
244bb flow rate=5 ml/min
Reactor=glass lined stainless steel with glass wool and rod support
1.2 g sintered Ni pellets Initially, conversion of 244bb was poor. The 244bb feed was switched off and after reducing the pellets with $H_2$ for a second time. Conversion temporarily increased to about 14% but the reaction was not very selective to 1234yf and 244bb conversion reduced significantly in under 3 hours. The 244bb feed was switched off and the pellets were treated with HCl (50% in $N_2$ for 2.5 hours at 400° C.), this increased 244bb conversion to 17% and the reaction was highly selective to 1234yf. Moreover, relatively high 244bb conversion and 1234yf selectivity were maintained for about 4 hours. The results are summarised below.

| Experiment Details/Events | Time/h | 244bb Conversion % | 1234yf Selectivity % | 1233xf Selectivity % |
|---|---|---|---|---|
| After 1st reduction | 0.5 | 2.56 | 69.92 | 20.20 |
|  | 3 days | 0.13 | 49.20 | 42.34 |
| After 2nd reduction | 0.5 | 13.85 | 38.21 | 38.84 |
|  | 3.0 | 0.48 | 65.95 | 34.05 |
| After HCl treatment | 1 | 17.08 | 98.17 | 1.05 |
|  | 4 | 15.62 | 98.57 | 0.86 |

The results show the surprising beneficial effect on conversion and, particularly, selectivity, for 244bb dehydrochlorination to 1234yf by chlorinating the catalyst prior to contacting it with the 244bb reagent stream.

The invention is defined by the following claims.

The invention claimed is:

1. A process for the preparation of a (hydro)(chloro)fluoroalkene, the process comprising:
   (i) contacting a reagent stream comprising a hydrochlorofluoroalkane with the catalyst in a reactor to dehydrochlorinate at least a portion of the hydrochlorofluoroalkane to produce a product stream comprising the (hydro)(chloro)fluoroalkene and HCl, wherein the catalyst is selected from the group consisting of metal oxide catalysts, metal halide catalysts, zero valent metal catalysts, carbon-based catalysts and mixtures thereof;
   (ii) chlorinating the catalyst prior to contacting the catalyst with the reagent stream; and/or carrying out step (i) in the presence of a HCl (hydrogen chloride) co-feed; and
   (iii) regenerating the catalyst by (a) regenerative oxidation or regenerative oxyfluorination and then by (b) regenerative chlorination.

2. A process according to claim 1, wherein step (i) the catalyst is chlorinated with a chlorinating agent comprising hydrogen chloride (HCl), chlorine ($Cl_2$), or a mixture thereof.

3. A process according to claim 1 wherein step (i) comprises contacting the catalyst with a chlorinating agent at a temperature of from about 200° C. to about 600° C.

4. A process according to claim 3 wherein the catalyst is contacted by a fluid stream of the chlorinating agent having a space velocity of from 0.1 $min^{-1}$ to about 3 $min^{-1}$ for about 1 hour to about 48 hours.

5. A process according to claim 2 wherein chlorinating agent is diluted by the presence of an inert gas, preferably wherein the inert gas is nitrogen.

6. A process according to claim 1, wherein the step (i) is combined with a catalyst drying step in a single procedure.

7. A process according to claim 1 wherein step (ii) the amount of HCl fed to the reactor is up to 50 mol % based on the combined amount of hydrochlorofluoroalkane and HCl fed to the reactor.

8. A process according to claim 1 wherein the amount of HCl fed to the reactor is at least 1 mol % based on the combined amount of hydrochlorofluoroalkane and HCl fed to the reactor.

9. A process according to claim 1 wherein at least a portion of the HCl in the product stream is recycled to the reactor to make up at least a portion of the HCl co-feed.

10. A process according to claim 1 wherein at least a portion of the HCl co-feed originates from a preceding process step of manufacturing the hydrochlorofluoroalkane.

11. A process according to claim 1 wherein the (hydro)(chloro)fluoroalkene is a $C_{3-7}$ (hydro)(chloro)fluoroalkene and the hydrochlorofluoroalkane is a $C_{3-7}$ hydrochlorofluoroalkane.

12. A process according to claim 11 wherein the $C_{3-7}$ (hydro)(chloro)fluoroalkene is a (hydro)(chloro)fluoropropene and the $C_{3-7}$ hydrochlorofluoroalkane is a hydrochlorofluoropropane.

13. A process according to claim 12 wherein the (hydro)(chloro)fluoropropene is a hydrochlorofluoropropene selected from the group consisting of 1-chloro-3,3,3-trifluoropropene ($CF_3CH=CHCl$, HCFO-1233zd) and 2-chloro-3,3,3-trifluoropropene ($CF_3CHCl=CH_2$, HCFO-1233xf).

14. A process according to claim 13 for preparing HCFO-1233zd, and wherein the hydrochlorofluoropropane is 1,1-dichloro-3,3,3-trifluoropropane ($CF_3CH_2CHCl_2$, HCFC-243fa).

15. A process according to claim 13 for preparing HCFO-1233xf, and wherein the hydrochlorofluoropropane is 1,2-dichloro-3,3,3-trifluoropropane ($CF_3CHClCH_2Cl$, HCFC-243db).

16. A process according to claim 12 wherein the (hydro)(chloro)fluoropropene is a hydrofluoropropene selected from the group consisting of 1,3,3,3-tetrafluoropropene ($CF_3CH=CHF$, HFO-1234ze) and 2,3,3,3-tetrafluoropropene ($CF_3CF=CH_2$, HFO-1234yf).

17. A process according to claim 16 for preparing HFO-1234yf, and wherein the hydrochlorofluoropropane is 2-chloro-1,1,1,2-tetrafluoropropane (HCFC-244bb).

18. A process according to claim 16 for preparing HFO-1234ze, and wherein the hydrochlorofluoropropane is 3-chloro-1,1,1,3-tetrafluoropropane (HCFC-244fa).

19. A process according to claim 1, wherein the catalyst comprises a metal oxide and wherein the metal is selected from the group consisting of Li, Na, K, Ca, Mg, Cs, Sc, Al, Y, Ti, Zr, Hf, V, Nb, Ta, Cr, Mo, W, Mn, Re, Fe, Ru, Co, Rh, Ir, Ni, Pd, Pt, Cu, Ag, Au, Zn, La and Ce.

20. A process according to claim 19 wherein the metal oxide comprises one or more of $Cr_2O_3$, $ZrO_2$, $Li_2O$, $Na_2O$, $K_2O$, CaO, MgO or $Cs_2O$.

21. A process according to claim 1, wherein the catalyst comprises a zinc/chromia catalyst.

22. A process according to claim 1, wherein the dehydrochlorination is carried out at a pressure of from about 0.1 to about 40 bara.

23. A process according to claim 1, wherein the dehydrochlorination is carried out at a temperature of from about 100° C. to about 600° C.

24. A process according to claim 1, wherein the reagent stream comprising a hydrochlorofluoroalkane contacting the catalyst has a space velocity of from about 0.1 min$^{-1}$ to about 10 min$^{-1}$.

25. A process according to claim 1 wherein the process is continuous, and wherein the catalyst is periodically regenerated by one or more of regenerative oxidation, regenerative oxyfluorination, regenerative reduction or regenerative chlorination.

26. A process according to claim 1 wherein the catalyst is regenerated by regenerative oxychlorination.

* * * * *